United States Patent [19]
Johnson

[11] Patent Number: 5,858,775
[45] Date of Patent: *Jan. 12, 1999

[54] ADENO-ASSOCIATED VIRUS MATERIALS AND METHODS

[75] Inventor: Philip R. Johnson, Gahanna, Ohio

[73] Assignee: Children's Hospital, Inc., Columbus, Ohio

[*] Notice: The term of this patent shall not extend beyond the expiration date of Pat. No. 5,658,785.

[21] Appl. No.: 709,609

[22] Filed: Sep. 10, 1996

Related U.S. Application Data

[62] Division of Ser. No. 254,358, Jun. 6, 1994, Pat. No. 5,658,785.

[51] Int. Cl.⁶ ............................ C12N 15/86; C07H 21/04
[52] U.S. Cl. .................. 435/320.1; 536/23.1; 536/23.72
[58] Field of Search ............................... 435/320.1, 172.1, 435/172.3, 240.2, 69.1, 325, 366; 536/23.1, 23.72

[56] References Cited

U.S. PATENT DOCUMENTS 4,797,368  1/1989  Carter et al. .......................... 435/320.1

FOREIGN PATENT DOCUMENTS

| WO 91/18088 | 11/1991 | WIPO . |
| WO 93/09239 | 5/1993 | WIPO . |
| WO 93/24641 | 12/1993 | WIPO . |
| WO 95/13365 | 5/1995 | WIPO . |
| WO 95/13392 | 5/1995 | WIPO . |
| WO 95/20671 | 8/1995 | WIPO . |
| WO 95/34670 | 12/1995 | WIPO . |

OTHER PUBLICATIONS

Berkemeier et al., "Neurotrophin–5: A Novel Neurotrophic Factor That Activates trk and trkB", *Neuron* 7:857–866 (1991).
Chatterjee et al., "Dual–Target Inhibition of HIV–1 in Vitro by Means of an Adeno–Associated Virus Antisense Vector", *Science* 258:1485–1488 (1992).
Dixit et al., "Construction and Expression of a Recombinant Adeno–Associated Virus That Harbors a Human β–Globin–Encoding cDNA", *Gene* 104:253–257 (1991).
Dutton, "Gene Therapy Likely to Target Cancer Patients on Larger Scale", *Genetic Engineering News* 14(1):1 and 14–15 (Jan. 15, 1994).
Flotte et al., "Gene Expression from Adeno–associated Virus Vectors in Airway Epithelial Cells", *Am. J. Respir. Cell Mol. Biol.* 7:349–356 (1992).
Flotte et al., "Expression of the Cystic Fibrosis Transmembrane Conductance Regulator from a Novel Adeno–associated Virus Promoter", *J. Biol. Chem.* 268(5):3781–3790 (1993).
Flotte et al., "An improved system for packaging recombinant adeno–associated virus vectors capable of in vivo transduction", *Gene Therapy* 2:29–37 (1995).
Furth et al., "Temporal Control of Gene Expression in Transgenic Mice by a Tetracycline–responsive Promoter", *Proc. Natl. Acad. Sci. (USA)* 91:9302–9306 (1994).
Grima et al., "A Single Human Gene Encoding Multiple Tyrosine Hydroxylases with Different Predicted Functional Characteristics", *Nature* 326:707–711 (1987).
Gossen et al., "Tight control of gene expression in mammalian cells by tetracycline–responsive promoters", *Proc. Natl. Acad. Sci. (USA)* 89:5547–5551 (1992).
Halbert et al., "Adeno–Associated Virus Vectors Transduce Primary Cells Much Less Efficiently than Immortalized Cells", *J. Virol.* 69(3):1473–1479 (1995).
Hermonat et al., "Use of Adeno–associated Virus as a Mammalian DNA Cloning Vector: Transduction of Neomycin Resistance into Mammalian Tissue Culture Cells", *Proc. Natl. Acad. Sci. (USA)* 81:6466–6470 (1984).
Hirsch et al., "An African primate lentivirus ($SIV_{sm}$) closely related to HIV–2", *Nature* 339:389–392 (1989).
Hirt, "Selective Extraction of Polyoma DNA from Infected Mouse Cell Cultures", *J. Mol. Biol.* 26:365–369 (1967).
Kaplitt et al., "Long–term gene expression and phenotypic correction using adeno–associated virus vectors in the mammalian brain", *Nature Genetics* 8:148–154 (1994).
Karasuyama et al., "Autocrine Growth and Tumorigenicity of Interleukin 2–Dependent Helper T Cells Transfected With IL–2 Gene", *J. Exp. Med.* 169:13–25 (1989).
Kotin et al., "Characterization of a Preferred Site of Human Chromosome 19q for Integration of Adeno–associated Virus DNA by Non–homologous Recombination", *EMBO J.* 11(13):5071–5078 (1992).
LaFace et al., "Gene Transfer into Hematopoietic Progenitor Cells Mediated by an Adeno–Associated Virus Vector", *Virol.* 162:483–486 (1988).
Lebkowski et al., "Adeno–Associated Virus: A Vector System for Efficient Introduction and Integration of DNA into a Variety of Mammalian Cell Types", *Mol. Cell. Biol.* 8:3988–3996 (1988).
Levi–Montalcini, "The Nerve Growth Factor 35 Years Later", *Science* 237:1154–1161 (1987).
Lin et al., "GDNF: A Glial Cell Line–Derived Neurotrophic Factor for Midbrain Dopaminergic Neurons", *Science* 260:1130–1132 (1993).
Maisonpierre et al., "Human and Rat Brain–Derived Neurotrophic Factor and Neurotrophin–3: Gene Structures, Distributions, and Chromosomal Localizations", *Genomics* 10:558–568 (1991).

(List continued on next page.)

*Primary Examiner*—David Guzo
*Attorney, Agent, or Firm*—Marshall, O'Toole, Gerstein, Murray & Borun

[57] ABSTRACT

The present invention provides adeno-associated virus (AAV) materials and methods which are useful for DNA delivery to cells. More particularly, the invention provides recombinant AAV (rAAV) genomes, methods for packaging rAAV genomes, stable host cell lines producing rAAV and methods for delivering genes of interest to cells utilizing the rAAV. Particularly disclosed are rAAV useful in generating immunity to human immunodeficiency virus-1 and in therapeutic gene delivery for treatment of neurological disorders.

4 Claims, 5 Drawing Sheets

OTHER PUBLICATIONS

Manthorpe et al., "Ciliary Neuronotrophic Factors", in *Nerve Growth Factors*, 35–56, Wiley & Sons (1989).

Muro–Cacho et al., "Gene Transfer in Human Lymphocytes Using a Vector Based on Adeno–Associated Virus", *J. Immunotherapy* 11:231–237 (1992).

Muzyczka, "Use of Adeno–Associated Virus as a General Transduction Vector for Mammalian Cells" in *Current Topics in Microbiology and Immunology* 158:97–129 (1992).

Podsakoff et al., "Efficient Gene Transfer into Nondividing Cells by Adeno–Associated Virus–Based Vectors", *J. Virol.* 68:5656–5666 (1994).

Puolakkainen et al., "Transforming Growth Factors Alpha and Beta", in *Neurotrophic Factors*, 359–389, Academic Press (1993).

Russell et al., "Adeno–associated virus vectors preferentially transduce cells in S phase", *Proc. Natl. Acad. Sci. (USA)* 91:8915–8919 (1994).

Samulski et al., "Helper–Free Stocks of Recombinant Adeno–Associated Viruses: Normal Integration Does Not Require Viral Gene Expression", *J. Virol.* 63:3822–3828 (1989).

Srivastava et al., "Nucleotide Sequence and Organization of the Adeno–Associated Virus 2 Genome", *J. Virol.* 45:555–564 (1983).

Sumi et al., "Characterization of Recombinant Human Aromatic L–Amino Acid Decarboxylase Expressed in COS Cells", *J. Neurochemistry* 55:1075–1078 (1990).

Tang et al., "Genetic immunization is a simple method for eliciting an immune response", *Nature* 356:152–154 (1992).

Tenenbaum et al., "Adeno–Associated Virus (AAV) as a Vector for Gene Transfer Into Glial Cells of the Human Central Nervous System", *Gene Therapy 1(Supplement 1)*:S80 (1994).

Tratschin et al., "Adeno–Associated Virus Vector for High–Frequency Integration Expression, and Rescue of Genes in Mammalian Cells", *Mol. Cell. Biol.* 5:3251–3260 (1985).

Ulmer et al., "Heterologous Protection Against Influenza by Injection of DNA Encoding a Viral Protein", *Science* 259:1475–1479 (1993).

Unsicker et al., "Fibroblast Growth Factors: Their Roles in the Central and PeripheraL Nervous System", in *Neurotrophic Factors*, 313–330, Academic Press (1993).

Vincent et al., "Replication and Packaging of HIV Envelope Genes in a Novel Adeno–associated Virus Vector System", *Vaccines* 90:353–359 (1990).

Warner et al., "Induction of HIV–Specific CTL and Antibody Responses in Mice Using Retroviral Vector–Transduced Cells", *AIDS Research and Human Retroviruses* 7:645–655 (1991).

Yu et al., "Progress towards gene therapy for HIV infection", *Gene Therapy* 1:13–26 (1994).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4680 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
TTGGCCACTC  CCTCTCTGCG  CGCTCGCTCG  CTCACTGAGG  CCGGGCGACC  AAAGGTCGCC     60
CGACGCCCGG  GCTTTGCCCG  GGCGGCCTCA  GTGAGCGAGC  GAGCGCGCAG  AGAGGGAGTG    120
GCCAACTCCA  TCACTAGGGG  TTCCTGGAGG  GGTGGAGTCG  TGACGTGAAT  TACGTCATAG    180
GGTTAGGGAG  GTCCTGTATT  AGAGGTCACG  TGAGTGTTTT  GCGACATTTT  GCGACACCAT    240
GTGGTCACGC  TGGGTATTTA  AGCCCGAGTG  AGCACGCAGG  GTCTCCATTT  TGAAGCGGGA    300
GGTTTGAACG  CGCAGCCGCC  ATGCCGGGGT  TTTACGAGAT  TGTGATTAAG  GTCCCCAGCG    360
ACCTTGACGG  GCATCTGCCC  GGCATTTCTG  ACAGCTTTGT  GAACTGGGTG  GCCGAGAAGG    420
AATGGGAGTT  GCCGCCAGAT  TCTGACATGG  ATCTGAATCT  GATTGAGCAG  GCACCCCTGA    480
CCGTGGCCGA  GAAGCTGCAG  CGCGACTTTC  TGACGGAATG  GCGCCGTGTG  AGTAAGGCCC    540
CGGAGGCCCT  TTTCTTTGTG  CAATTTGAGA  AGGGAGAGAG  CTACTTCCAC  ATGCACGTGC    600
TCGTGGAAAC  CACCGGGGTG  AAATCCATGG  TTTTGGGACG  TTTCCTGAGT  CAGATTCGCG    660
AAAAACTGAT  TCAGAGAATT  TACCGCGGGA  TCGAGCCGAC  TTTGCCAAAC  TGGTTCGCGG    720
TCACAAAGAC  CAGAAATGGC  GCCGGAGGCG  GGAACAAGGT  GGTGGATGAG  TGCTACATCC    780
CCAATTACTT  GCTCCCCAAA  ACCCAGCCTG  AGCTCCAGTG  GGCGTGGACT  AATATGGAAC    840
AGTATTTAAG  CGCCTGTTTG  AATCTCACGG  AGCGTAAACG  GTTGGTGGCG  CAGCATCTGA    900
CGCACGTGTC  GCAGACGCAG  GAGCAGAACA  AAGAGAATCA  GAATCCCAAT  TCTGATGCGC    960
CGGTGATCAG  ATCAAAAACT  TCAGCCAGGT  ACATGGAGCT  GGTCGGGTGG  CTCGTGGACA   1020
AGGGGATTAC  CTCGGAGAAG  CAGTGGATCC  AGGAGGACCA  GGCCTCATAC  ATCTCCTTCA   1080
ATGCGGCCTC  CAACTCGCGG  TCCCAAATCA  AGGCTGCCTT  GGACAATGCG  GGAAAGATTA   1140
TGAGCCTGAC  TAAAACCGCC  CCCGACTACC  TGGTGGGCCA  GCAGCCCGTG  GAGGACATTT   1200
```

```
CCAGCAATCG GATTTATAAA ATTTTGGAAC TAAACGGGTA CGATCCCCAA TATGCGGCTT   1260
CCGTCTTTCT GGGATGGGCC ACGAAAAAGT TCGGCAAGAG GAACACCATC TGGCTGTTTG   1320
GGCCTGCAAC TACCGGGAAG ACCAACATCG CGGAGGCCAT AGCCCACACT GTGCCCTTCT   1380
ACGGGTGCGT AAACTGGACC AATGAGAACT TTCCCTTCAA CGACTGTGTC GACAAGATGG   1440
TGATCTGGTG GGAGGAGGGG AAGATGACCG CCAAGGTCGT GGAGTCGGCC AAAGCCATTC   1500
TCGGAGGAAG CAAGGTGCGC GTGGACCAGA AATGCAAGTC CTCGGCCCAG ATAGACCCGA   1560
CTCCCGTGAT CGTCACCTCC AACACCAACA TGTGCGCCGT GATTGACGGG AACTCAACGA   1620
CCTTCGAACA CCAGCAGCCG TTGCAAGACC GGATGTTCAA ATTTGAACTC ACCCGCCGTC   1680
TGGATCATGA CTTTGGGAAG GTCACCAAGC AGGAAGTCAA AGACTTTTTC CGTGGGCAA   1740
AGGATCACGT GGTTGAGGTG GAGCATGAAT TCTACGTCAA AAAGGGTGGA GCCAAGAAAA   1800
GACCCGCCCC CAGTGACGCA GATATAAGTG AGCCCAAACG GGTGCGCGAG TCAGTTGCGC   1860
AGCCATCGAC GTCAGACGCG GAAGCTTCGA TCAACTACGC AGACAGGTAC CAAAACAAAT   1920
GTTCTCGTCA CGTGGGCATG AATCTGATGC TGTTTCCCTG CAGACAATGC GAGAGAATGA   1980
ATCAGAATTC AAATATCTGC TTCACTCACG GACAGAAAGA CTGTTTAGAG TGCTTTCCCG   2040
TGTCAGAATC TCAACCCGTT TCTGTCGTCA AAAGGCGTA TCAGAAACTG TGCTACATTC   2100
ATCATATCAT GGGAAAGGTG CCAGACGCTT GCACTGCCTG CGATCTGGTC AATGTGGATT   2160
TGGATGACTG CATCTTTGAA CAATAAATGA TTTAAATCAG GTATGGCTGC CGATGGTTAT   2220
CTTCCAGATT GGCTCGAGGA CACTCTCTCT GAAGGAATAA GACAGTGGTG GAAGCTCAAA   2280
CCTGGCCCAC CACCACCAAA GCCCGCAGAG CGGCATAAGG ACGACAGCAG GGTCTTGTG   2340
CTTCCTGGGT ACAAGTACCT CGGACCCTTC AACGGACTCG ACAAGGGAGA GCCGGTCAAC   2400
GAGGCAGACG CCGCGGCCCT CGAGCACGAC AAAGCCTACG ACCGGCAGCT CGACAGCGGA   2460
GACAACCCGT ACCTCAAGTA CAACCACGCC GACGCGGAGT TTCAGGAGCG CCTTAAAGAA   2520
GATACGTCTT TTGGGGGCAA CCTCGGACGA GCAGTCTTCC AGGCGAAAAA GAGGGTTCTT   2580
GAACCTCTGG GCCTGGTTGA GGAACCTGTT AAGACGGCTC CGGGAAAAAA GAGGCCGGTA   2640
GAGCACTCTC CTGTGGAGCC AGACTCCTCC TCGGGAACCG GAAAGGCGGG CCAGCAGCCT   2700
GCAAGAAAAA GATTGAATTT TGGTCAGACT GGAGACGCAG ACTCAGTACC TGACCCCCAG   2760
CCTCTCGGAC AGCCACCAGC AGCCCCTCT GGTCTGGGAA CTAATACGAT GGCTACAGGC   2820
AGTGGCGCAC CAATGGCAGA CAATAACGAG GGCGCCGACG GAGTGGGTAA TTCCTCCGGA   2880
AATTGGCATT GCGATTCCAC ATGGATGGGC GACAGAGTCA TCACCACCAG CACCCGAACC   2940
TGGGCCCTGC CCACCTACAA CAACCACCTC TACAAACAAA TTTCCAGCCA ATCAGGAGCC   3000
TCGAACGACA ATCACTACTT TGGCTACAGC ACCCCTTGGG GGTATTTTGA CTTCAACAGA   3060
TTCCACTGCC ACTTTTCACC ACGTGACTGG CAAAGACTCA TCAACAACAA CTGGGGATTC   3120
CGACCCAAGA GACTCAACTT CAAGCTCTTT AACATTCAAG TCAAAGAGGT CACGCAGAAT   3180
GACGGTACGA CGACGATTGC CAATAACCTT ACCAGCACGG TTCAGGTGTT TACTGACTCG   3240
GAGTACCAGC TCCCGTACGT CCTCGGCTCG GCGCATCAAG GATGCCTCCC GCCGTTCCCA   3300
GCAGACGTCT TCATGGTGCC ACAGTATGGA TACCTCACCC TGAACAACGG GAGTCAGGCA   3360
GTAGGACGCT CTTCATTTTA CTGCCTGGAG TACTTTCCTT CTCAGATGCT GCGTACCGGA   3420
AACAACTTTA CCTTCAGCTA CACTTTTGAG GACGTTCCTT TCCACAGCAG CTACGCTCAC   3480
AGCCAGAGTC TGGACCGTCT CATGAATCCT CTCATCGACC AGTACCTGTA TTACTTGAGC   3540
AGAACAAACA CTCCAAGTGG AACCACCACG CAGTCAAGGC TTCAGTTTTC TCAGGCCGGA   3600
```

| | | | | | | |
|---|---|---|---|---|---|---|
| GCGAGTGACA | TTCGGGACCA | GTCTAGGAAC | TGGCTTCCTG | GACCCTGTTA | CCGCCAGCAG | 3660 |
| CGAGTATCAA | AGACATCTGC | GGATAACAAC | AACAGTGAAT | ACTCGTGGAC | TGGAGCTACC | 3720 |
| AAGTACCACC | TCAATGGCAG | AGACTCTCTG | GTGAATCCGG | GGCCCGCCAT | GGCAAGCCAC | 3780 |
| AAGGACGATG | AAGAAAGTT | TTTTCCTCAG | AGCGGGGTTC | TCATCTTTGG | GAAGCAAGGC | 3840 |
| TCAGAGAAAA | CAAATGTGAA | CATTGAAAAG | GTCATGATTA | CAGACGAAGA | GGAAATCGGA | 3900 |
| ACAACCAATC | CCGTGGCTAC | GGAGCAGTAT | GGTTCTGTAT | CTACCAACCT | CCAGAGAGGC | 3960 |
| AACAGACAAG | CAGCTACCGC | AGATGTCAAC | ACACAAGGCG | TTCTTCCAGG | CATGGTCTGG | 4020 |
| CAGGACAGAG | ATGTGTACCT | TCAGGGGCCC | ATCTGGGCAA | AGATTCCACA | CACGGACGGA | 4080 |
| CATTTTCACC | CCTCTCCCCT | CATGGGTGGA | TTCGGACTTA | AACACCCTCC | TCCACAGATT | 4140 |
| CTCATCAAGA | ACACCCCGGT | ACCTGCGAAT | CCTTCGACCA | CCTTCAGTGC | GGCAAAGTTT | 4200 |
| GCTTCCTTCA | TCACACAGTA | CTCCACGGGA | CACGGTCAGC | GTGGAGATCG | AGTGGGAGCT | 4260 |
| GCAGAAGGAA | AACAGCAAAC | GCTGGAATCC | CGAAATTCAG | TACACTTCCA | ACTACAACAA | 4320 |
| GTCTGTTAAT | CGTGGACTTA | CCGTGGATAC | TAATGGCGTG | TATTCAGAGC | CTCGCCCCAT | 4380 |
| TGGCACCAGA | TACCTGACTC | GTAATCTGTA | ATTGCTTGTT | AATCAATAAA | CCGTTTAATT | 4440 |
| CGTTGCAGTT | GAACTTTGGT | CTCTGCGTAT | TTCTTTCTTA | TCTAGTTTCC | ATGGCTACGT | 4500 |
| AGATAATTAG | CATGGCGGGT | TAATCATTAA | CTACAAGGAA | CCCCTAGTGA | TGGAGTTGGC | 4560 |
| CACTCCCTCT | CTGCGCGCTC | GCTCGCTCAC | TGAGGCCGGG | CGACCAAAGG | TCGCCCGACG | 4620 |
| CCCGGGCTTT | GCCCGGGCGG | CCTCAGTGAG | CGAGCGAGCG | CGCAGAGAGG | GAGTGGCCAA | 4680 |

( 2 ) INFORMATION FOR SEQ ID NO:2:

( i ) SEQUENCE CHARACTERISTICS:
        ( A ) LENGTH: 2658 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| ATGGGATGTC | TTGGGAATCA | GCTGCTTATC | GCGCTCTTGC | TAGTAAGTGT | TTTAGAGATT | 60 |
| TGTTGTGTTC | AATATGTAAC | AGTATTCTAT | GGTGTACCAG | CATGGAAGAA | TGCGACAATT | 120 |
| CCCCTCTTCT | GTGCAACCAA | GAATAGGGAC | ACTTGGGGAA | CAACACAATG | CTTGCCAGAT | 180 |
| AATGATGATT | ACTCAGAATT | GGCAATCAAT | GTCACAGAGG | CTTTTGATGC | TTGGGATAAT | 240 |
| ACAGTCACAG | AACAAGCAAT | AGAGGATGTG | TGGAACCTCT | TTGAAACATC | CATTAAGCCC | 300 |
| TGTGTAAAAC | TCACCCCACT | ATGTATAGCA | ATGAGATGTA | ATAAAACTGA | GACAGATAGG | 360 |
| TGGGGTTTGA | CAGGAAACGC | AGGGACAACA | ACAACAGCAA | TAACAACAAC | AGCAACACCA | 420 |
| AGTGTAGCAG | AAAATGTTAT | AAATGAAAGT | AATCCGGGCA | TAAAAAATAA | TAGTTGTGCA | 480 |
| GGCTTGGAAC | AGGAGCCCAT | GATAGGTTGT | AAATTTAACA | TGACAGGGTT | AAATAGGGAC | 540 |
| AAAAAGAAAG | AATATAATGA | AACATGGTAT | TCAAGAGATT | TAATCTGTGA | GCAGTCAGCG | 600 |
| AATGAAAGTG | AGAGTAAATG | TTACATGCAT | CATTGTAACA | CCAGTGTTAT | TCAAGAATCC | 660 |
| TGTGACAAGC | ATTATTGGGA | TGCTATTAGA | TTTAGATACT | GTGCACCGCC | AGGTTATGCT | 720 |
| TTGCTTAGGT | GTAATGATTC | AAATTATTTA | GGCTTTGCTC | CTAACTGTTC | TAAGGTAGTG | 780 |
| GTTTCTTCAT | GCACAAGAAT | GATGGAGACG | CAAACCTCTA | CTTGGTTTGG | CTTCAATGGT | 840 |
| ACTAGGGCAG | AAAATAGAAC | ATACATTTAT | TGGCATGGCA | AAAGTAATAG | AACCATAATT | 900 |
| AGCTTGAATA | AGTATTATAA | TCTAACAATG | AGATGTAGAA | GACCAGAAAA | TAAGACAGTT | 960 |

-continued

```
TTACCAGTCA CCATTATGTC AGGGTTGGTC TTCCATTCGC AGCCCATAAA TGAGAGACCA      1020

AAACAGGCCT GGTGCTGGTT TGAAGGAAGC TGGAAAAAGG CCATCCAGGA AGTGAAGGAA      1080

ACCTTGGTCA AACATCCCAG GTATACGGGA ACTAATGATA CTAGGAAAAT TAATCTAACA      1140

GCTCCAGCAG GAGGAGATCC AGAAGTCACT TTTATGTGGA CAAATTGTCG AGGAGAATTC      1200

TTATATTGCA AAATGAATTG GTTTCTTAAT TGGGTAGAGG ACAGAGACCA AAAGGGTGGC      1260

AGATGGAAAC AACAAAATAG GAAAGAGCAA CAGAAGAAAA ATTATGTGCC ATGTCATATT      1320

AGACAAATAA TCAACACGTG GCACAAAGTA GGCAAAAATG TATATTTGCC TCCTAGGGAA      1380

GGAGACCTGA CATGCAATTC CACTGTAACT AGTCTCATAG CAGAGATAGA TTGGATCAAT      1440

AGCAATGAGA CCAATATCAC CATGAGTGCA GAGGTGGCAG AACTGTATCG ATTGGAGTTG      1500

GGAGATTACA AATTAATAGA GATTACTCCA ATTGGCTTGG CCCCCACAAG TGTAAGAAGG      1560

TACACCACAA CTGGTGCCTC AAGAAATAAG AGAGGGGTCT TTGTGCTAGG GTTCTTGGGT      1620

TTTCTCGCGA CAGCAGGTTC TGCAATGGGC GCGGCGTCCG TGACGCTGTC GGCTCAGTCC      1680

CGGACTTTGT TGGCTGGGAT AGTGCAGCAA CAGCAACAGC TGTTGGATGT GGTCAAGAGA      1740

CAACAAGAAT TGTTGCGACT GACCGTCTGG GGAACTAAGA ACCTCCAGAC TAGAGTCACT      1800

GCTATCGAGA AGTACCTGAA GGATCAGGCG CAGCTAAATT CATGGGGATG TGCTTTTAGG      1860

CAAGTCTGTC ACACTACTGT ACCATGGCCA AATGAAACAT TGGTGCCTAA TTGGAACAAT      1920

ATGACTTGGC AAGAGTGGGA AAGACAGGTT GACTTCCTAG AGGCAAATAT AACTCAATTA      1980

TTAGAAGAAG CACAAATTCA GCAAGAAAAG AATATGTATG AATTGCAAAA ATTAAATAGC      2040

TGGGATATCT TTGGCAATTG GTTTGACCTT ACTTCTTGGA TAAGATATAT ACAATATGGT      2100

GTACTTATAG TTCTAGGAGT AATAGGGTTA AGAATAGTAA TATATGTAGT GCAAATGTTA      2160

GCTAGGTTAA GACAGGGTTA TAGGCCAGTG TTCTCTTCCC CTCCCGCTTA TGTTCAGCAG      2220

ATCCCTATCC ACAAGGGCCA GGAACCGCCA ACCAAAGAAG GAGAAGAAGG AGACGGTGGA      2280

GACAGAGGTG GCAGCAGATC TTGGCCTTGG CAGATAGAAT ATATTCATTT CCTGATCCGC      2340

CAGTTGATAC GCCTCTTGAC TTGGCTATTC AGCAGCTGCA GGGATTGGCT ATTGAGGAGC      2400

TACCAGATCC TCCAACCAGT GCTCCAGAGC CTCTCAACGA CGTTGCAAAG AGTCCGTGAA      2460

GTCATCAGAA TTGAAATAGC CTACCTACAA TATGGGTGGC GCTATTTCCA AGAAGCAGTA      2520

CAAGCGTGGT GGAAACTTGC GCGAGAGACT CTTGCAAGCG CGTGGGGAGA CATATGGGAG      2580

ACTCTGGGAA GGGTTGGAAG AGGGATACTC GCAATCCCTA GGCGCATCAG GCAAGGGCTT      2640

GAGCTCACTC TCTTGTGA                                                    2658
```

( 2 ) INFORMATION FOR SEQ ID NO:3:

( i ) SEQUENCE CHARACTERISTICS:
        ( A ) LENGTH: 2571 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATGAGAGTGA AGGGGATCAG GAGGAATTAT CAGCACTGGT GGGGATGGGG CACGATGCTC       60

CTTGGGTTAT TAATGATCTG TAGTGCTACA GAAAAATTGT GGGTCACAGT CTATTATGGG      120

GTACCTGTGT GGAAAGAAGC AACCACCACT CTATTTTGTG CATCAGATGC TAAAGCATAT      180

GATACAGAGG TACATAATGT TTGGGCCACA CAAGCCTGTG TACCCACAGA CCCCAACCCA      240
```

| | | | | | | |
|---|---|---|---|---|---|---|
| CAAGAAGTAG | AATTGGTAAA | TGTGACAGAA | AATTTTAACA | TGTGGAAAAA | TAACATGGTA | 300 |
| GAACAGATGC | ATGAGGATAT | AATCAGTTTA | TGGGATCAAA | GCCTAAAGCC | ATGTGTAAAA | 360 |
| TTAACCCCAC | TCTGTGTTAC | TTTAAATTGC | ACTGATTTGA | GGAATACTAC | TAATACCAAT | 420 |
| AATAGTACTG | CTAATAACAA | TAGTAATAGC | GAGGGAACAA | TAAAGGGAGG | AGAAATGAAA | 480 |
| AACTGCTCTT | TCAATATCAC | CACAAGCATA | AGAGATAAGA | TGCAGAAAGA | ATATGCACTT | 540 |
| CTTTATAAAC | TTGATATAGT | ATCAATAGAT | AATGATAGTA | CCAGCTATAG | GTTGATAAGT | 600 |
| TGTAATACCT | CAGTCATTAC | ACAAGCTTGT | CCAAAGATAT | CCTTTGAGCC | AATTCCCATA | 660 |
| CACTATTGTG | CCCCGGCTGG | TTTTGCGATT | CTAAATGTA | ACGATAAAAA | GTTCAGTGGA | 720 |
| AAAGGATCAT | GTAAAAATGT | CAGCACAGTA | CAATGTACAC | ATGGAATTAG | GCCAGTAGTA | 780 |
| TCAACTCAAC | TGCTGTTAAA | TGGCAGTCTA | GCAGAAGAAG | AGGTAGTAAT | TAGATCTGAG | 840 |
| AATTTCACTG | ATAATGCTAA | AACCATCATA | GTACATCTGA | ATGAATCTGT | ACAAATTAAT | 900 |
| TGTACAAGAC | CCAACTACAA | TAAAAGAAAA | AGGATACATA | TAGGACCAGG | GAGAGCATTT | 960 |
| TATACAACAA | AAAATATAAT | AGGAACTATA | AGACAAGCAC | ATTGTAACAT | TAGTAGAGCA | 1020 |
| AAATGGAATG | ACACTTTAAG | ACAGATAGTT | AGCAAATTAA | AGAACAATT | TAAGAATAAA | 1080 |
| ACAATAGTCT | TTAATCAATC | CTCAGGAGGG | GACCCAGAAA | TTGTAATGCA | CAGTTTTAAT | 1140 |
| TGTGGAGGGG | AATTTTTCTA | CTGTAATACA | TCACCACTGT | TTAATAGTAC | TTGGAATGGT | 1200 |
| AATAATACTT | GGAATAATAC | TACAGGGTCA | AATAACAATA | TCACACTTCA | ATGCAAAATA | 1260 |
| AAACAAATTA | TAAACATGTG | GCAGGAAGTA | GGAAAAGCAA | TGTATGCCCC | TCCCATTGAA | 1320 |
| GGACAAATTA | GATGTTCATC | AAATATTACA | GGGCTACTAT | TAACAAGAGA | TGGTGGTAAG | 1380 |
| GACACGGACA | CGAACGACAC | CGAGATCTTC | AGACCTGGAG | GAGGAGATAT | GAGGGACAAT | 1440 |
| TGGAGAAGTG | AATTATATAA | ATATAAAGTA | GTAACAATTG | AACCATTAGG | AGTAGCACCC | 1500 |
| ACCAAGGCAA | AGAGAAGAGT | GGTGCAGAGA | GAAAAAAGAG | CAGCGATAGG | AGCTCTGTTC | 1560 |
| CTTGGGTTCT | TAGGAGCAGC | AGGAAGCACT | ATGGGCGCAG | CGTCAGTGAC | GCTGACGGTA | 1620 |
| CAGGCCAGAC | TATTATTGTC | TGGTATAGTG | CAACAGCAGA | ACAATTTGCT | GAGGGCCATT | 1680 |
| GAGGCGCAAC | AGCATATGTT | GCAACTCACA | GTCTGGGGCA | TCAAGCAGCT | CCAGGCAAGA | 1740 |
| GTCCTGGCTG | TGGAAAGATA | CCTAAAGGAT | CAACAGCTCC | TGGGGTTTTG | GGGTTGCTCT | 1800 |
| GGAAAACTCA | TTTGCACCAC | TACTGTGCCT | TGGAATGCTA | GTTGGAGTAA | TAAATCTCTG | 1860 |
| GATGATATTT | GGAATAACAT | GACCTGGATG | CAGTGGGAAA | GAGAAATTGA | CAATTACACA | 1920 |
| AGCTTAATAT | ACTCATTACT | AGAAAAATCG | CAAACCCAAC | AAGAAAAGAA | TGAACAAGAA | 1980 |
| TTATTGGAAT | TGGATAAATG | GGCAAGTTTG | TGGAATTGGT | TTGACATAAC | AAATTGGCTG | 2040 |
| TGGTATATAA | AAATATTCAT | AATGATAGTA | GGAGGCTTGG | TAGGTTTAAG | AATAGTTTTT | 2100 |
| GCTGTACTTT | CTATAGTGAA | TAGAGTTAGG | CAGGGATACT | CACCATTGTC | GTTGCAGACC | 2160 |
| CGCCCCCCAG | TTCCGAGGGG | ACCCGACAGG | CCCGAAGGAA | TCGAAGAAGA | AGGTGGAGAG | 2220 |
| AGAGACAGAG | ACACATCCGG | TCGATTAGTG | CATGGATTCT | TAGCAATTAT | CTGGGTCGAC | 2280 |
| CTGCGGAGCC | TGTTCCTCTT | CAGCTACCAC | CACAGAGACT | TACTCTTGAT | TGCAGCGAGG | 2340 |
| ATTGTGGAAC | TTCTGGGACG | CAGGGGGTGG | GAAGTCCTCA | AATATTGGTG | GAATCTCCTA | 2400 |
| CAGTATTGGA | GTCAGGAACT | AAAGAGTAGT | GCTGTTAGCT | TGCTTAATGC | CACAGCTATA | 2460 |
| GCAGTAGCTG | AGGGGACAGA | TAGGGTTATA | GAAGTACTGC | AAAGAGCTGG | TAGAGCTATT | 2520 |
| CTCCACATAC | CTACAAGAAT | AAGACAGGGC | TTGGAAAGGG | CTTTGCTATA | A | 2571 |

ADENO-ASSOCIATED VIRUS MATERIALS AND METHODS

This is a divisional of U.S. application Ser. No. 08/254,358, filed Jun. 6, 1994 now U.S. Pat. No. 5,658,785.

FIELD OF THE INVENTION

The present invention generally relates to adeno-associated virus (AAV) materials and methods which are useful for delivering DNA to cells. More particularly, the invention relates to recombinant AAV (rAAV) genomes, to methods for packaging rAAV genomes, to stable cell lines producing rAAV and to methods for delivering genes of interest to cells utilizing the rAAV.

BACKGROUND

Adeno-associated virus (AAV) is a replication-deficient parvovirus, the single-stranded DNA genome of which is about 4.7 kb in length including 145 nucleotide inverted terminal repeat (ITRs). See FIG. 1. The nucleotide sequence of the AAV2 genome is presented in Srivastava et al., *J. Virol.*, 45: 555–564 (1983). Cis-acting sequences directing viral DNA replication (ori), encapsidation/packaging (pkg) and host cell chromosome integration (int) are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97–129 (1992).

When AAV infects a human cell, the viral genome integrates into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive as a vector for delivering foreign DNA to cells. AAV infection of cells in culture is noncytopathic, and natural infection of humans and other animals is silent and asymptomatic. Moreover, AAV infects most (if not all) mammalian cells allowing the possibility of targeting many different tissues in vivo. Kotin et al, *EMBO J.*, 11(13): 5071–5078 (1992) reports that the DNA genome of AAV undergoes targeted integration on chromosome 19 upon infection. Replication of the viral DNA is not required for integration, and thus helper virus is not required for this process. The AAV proviral genome is infectious as cloned DNA in plasmids which makes construction of recombinant genomes feasible. Furthermore, because the signals directing AAV replication, genome encapsidation and integration are contained within the ITRs of the AAV genome, the internal approximately 4.3 kb of the genome (encoding replication and structural capsid proteins, rep-cap) may thus be replaced with foreign DNA such as a gene cassette containing a promoter, a DNA of interest and a polyadenylation signal. Another significant feature of AAV is that it is an extremely stable and hearty virus. It easily withstands the conditions used to inactivate adenovirus (56° to 65° C. for several hours), making cold preservation of rAAV-based vaccines less critical. Finally, AAV-infected cells are not resistant to superinfection.

Various groups have studied the potential use of AAV in treatment of disease states. Patent Cooperation Treaty (PCT) Internation Publication No. WO 91/18088 published Nov. 28, 1991 and the corresponding journal article by Chatterjee et al., *Science*, 258: 1485–1488 (1992) describe the transduction of intracellular resistance to human immunodeficiency virus-i (HIV-1) in human hematopoietic and non-hematopoietic cell lines using an rAAV encoding an antisense RNA specific for the HIV-1 TAR sequence and polyadenylation signal. The review article Yu et al., *Gene Therapy*, 1: 13–26 (1994) concerning gene therapy for HIV-1 infection lists AAV as a possible gene therapy vector for hematopoietic stem cells. The use of rAAV vectors as a delivery system for stable integration and expression of genes (in particular the cystic fibrosis transmembrane regulator gene) in cultured airway epithelial cells is described in PCT International Publication No. WO 93/24641 published Dec. 9, 1993 and in the corresponding journal article by Flotte et al., *Am. J. Respir. Cell Mol. Biol.*, 7: 349–356 (1992). Gene therapy involving rAAV in the treatment of hemoglobinopathies and other hematopoietic diseases and in conferring cell-specific multidrug resistance is proposed in PCT International Publication No. WO 93/09239 published May 13, 1993; Muro-Cacho et al., *J. Immunol.*, 11: 231–237 (1992); LaFace et al., *Virol.*, 162: 483–486 (1988); and Dixit et al., *Gene*, 104: 253–257 (1991). Therapeutic gene delivery into glioma cells is proposed in Tenenbaum et al., *Gene Therapy*, 1 (Supplement 1): S80 (1994).

A reletively new concept in the field of gene transfer is that immunization may be effected by the product of a transfered gene. Several attempts at "genetic immunization" have been reported including direct DNA injection of influenza A nucleoprotein sequences [Ulmer et al., *Science*, 259: 1475–1749 (1993)], biolistic gun immunization with human growth hormone sequences [Tang et al., *Nature*, 356: 152–154 (1992) and infection with retroviral vectors containing HIV-1 gp160 envelope protein sequences [Warner et al., *AIDS RESEARCH AND HUMAN RETROVIRUSES*, 7(8): 645–655 (1991)]. While these approaches appear to be feasible, direct DNA inoculation may not provide long-lasting immune responses and serious questions of safety surround the use of retroviral vectors. The use of AAV for genetic immunization is a novel approach that is not subject to these problems.

An obstacle to the use of AAV for delivery of DNA is the lack of highly efficient schemes for encapsidation of recombinant genomes. Several methods have been described for encapsidating rAAV genomes to generate recombinant viral particles. These methods all require in trans AAV rep-cap and adenovirus helper functions. The simplest involves transfecting the rAAV genome into host cells followed by co-infection with wild-type AAV and adenovirus. See, for example, U.S. Pat. No. 4,797,368 issued Jan. 10, 1989 to Carter and Tratschin, and the corresponding journal article by Tratschin et al., *Mol. Cell. Biol.*, 5(11): 3251–3260 (1985). This method, however, leads to unacceptably high levels of wild-type AAV. Another general strategy involves supplying the AAV functions on a second plasmid (separate from the rAAV genome) that is co-transfected with the rAAV plasmid. See, for example, Hermonat et al., *Proc. Natl. Acad. Sci. USA*, 81: 6466–6470 (1984) and Lebkowski et al., *Mol. Cell. Biol.*, 8(10): 3988–3996 (1988). If no sequence overlap exists between the two plasmids, then wild-type AAV production is avoided as is described in Samulski et al., *J. Virol.*, 63(9): 3822–3828 (1989). This strategy is inherently inefficient, however, due to the requirement for three separate DNA transfer events (co-transfection of two plasmids as well as infection with adenovirus) to generate rAAV particles. Large scale production of rAAV by this method is costly and is subject to variations in transfection efficiency.

Vincent et al., *Vaccines*, 90: 353–359 (1990) reports that a cell line expressing rep-cap functions could be used to package rAAV. Such methods still requires transfection of the rAAV genome into the cell line and the resulting titer of rAAV reported was very low (only about $10^3$ infectious units/ml). Dutton, *Genetic Engineering News*, 14(1): 1 and 14–15 (Jan. 15, 1994) reports that Dr. Jane Lebkowski of Applied Immune Sciences manufactures rAAV using chimeric AAV/Epstein-Barr virus plasmids that contain a recombinant AAV genome, the hygromycin resistance gene and the EBV ori P fragment and EBNA gene. The plasmids are transfected into cells to generate stable cell lines. The stable cell lines are then transfected with wild-type AAV rep-cap functions and infected with adenovirus to produce rAAV. Like the method of Vincent, the Lebkowski packaging method requires both transfection and infection events to generate rAAV particles.

There thus exists a need in the art for efficient methods of packaging rAAV genomes and for specific rAAVs useful as vectors for DNA delivery to cells.

SUMMARY OF THE INVENTION

The present invention provides recombinant AAV (rAAV) genomes useful for delivering non-AAV DNA of interest to a cell. The rAAV genomes of the invention include AAV ITRs flanking non-AAV DNA sequences of interest and lack rep-cap sequences encoding functional rep-cap proteins. If it is desirable to express the DNA of interest as a polypeptide in the cell, the rAAV genome also includes a (constitutive or regulatable) promoter and a polyadenylation signal operably linked to the DNA of interest to form a gene cassette. The gene cassette may also include intron sequences to facilitate processing of the RNA transcript in mammalian host cells. A presently preferred gene cassette includes the following DNA segments: (1) the cytomegalovirus (CMV) immediate early promoter, (2) the rabbit β-globin intron, (3) simian immunodeficiency virus (SIV) or human immunodeficiency (HIV) rev and envelope (gp160) genes, and (4) the rabbit β-globin polyadenylation signal. The rAAV genomes of the invention may be assembled in vectors useful for transfection of cells which are permissible for infection with a helper virus of AAV (e.g., adenovirus, E1-deleted adenovirus or herpesvirus). A vector of the invention which contains a rAAV genome including the foregoing preferred gene cassette, a neomycin resistance gene, and wild-type AAV rep-cap sequences was deposited in *E. coli* DH5 cells with the American Type Culture Collection (ATCC), 12301 Parklawn Drive, Rockville, Md. 20852, on Jun. 1, 1994 and was assigned ATCC Accession No. 69637.

Presently preferred rAAV genomes include the SIV rev and envelope (gp160) genes, or the HIV rev and envelope genes, as the non-AAV DNA(s) of interest. Also preferred are rAAV genomes which contain sequences encoding proteins which may ameliorate neurological disorders such as: sequences encoding nerve growth factor (NGF), ciliary neurotrophic factor (CNTF), brain-derived neurotrophic factor (BDNF), neurotrophins 3 and 4/5 (NT-3 and 4/5), glial cell derived neurotrophic factor (GDNF), transforming growth factors (TGF), and acidic and basic fibroblast growth factor (a and bFGF); sequences enoding tyrosine hydroxylase (TH) and aromatic amino acid decarboxylase (AADC); sequences encoding superoxide dimutase (SOD 1 or 2), catalase and glutathione peroxidase; sequences encoding interferons, lymphokines, cytokines and antagonists thereof such as tumor necrosis factor (TNF), CD4 specific antibodies, and TNF or CD4 receptors; sequences encoding GABA receptor isolforms, the GABA synthesizing enzyme glutamic acid decarboxylase (GAD), calcium dependent potassium channels or ATP-sensitive potassium channels; and sequences encoding thymidine kinase. Recombinant AAV genomes including antisense nucleotides that affect expression of certain genes such as cell death supressor genes (e.g., bcl-2) or that affect expression of excitatory amino acid receptors (e.g., glutamate and NMDA receptors) are also contemplated for modulating neurological disorders.

Other DNA sequences of interest contemplated by the invention include sequences from pathogens including: HIV-1 and HIV-2 (sequences other than rev and gp160 sequences); human T-lymphotrophic virus types I and II; respiratory syncytial virus; parainfluenza virus types 1–4; measles virus; mumps virus; rubella virus; polio viruses types 1–3; influenza virus types A, B and C; non-human influenza viruses (avian, equine, porcine); hepatitis virus types A, B, C, D and E; rotavirus; norwalk virus; cytomegaloviruses; Epstein-Barr virus; herpes simplex virus types 1 and 2; varicella-zoster virus; human herpes virus type 6; hantavirus; adenoviruses; chlamydia pneumoniae; chlamydia trachomatis; mycoplasma pneumoniae; mycobacterium tuberculosis; atypical mycobacteria; feline leukemia virus; feline immunodeficiency virus; bovine immunodeficiency virus; equine infectious anemia virus; caprine arthritis encephalitis virus; and visna virus.

Cell lines of the invention are stably transfected with both rAAV genomes of the invention and with copies of the AAV rep and cap genes. Preferred cell lines are mammalian cell lines, for example, HeLa cell lines or 293 cell lines. Infection of the cell lines of the invention with AAV helper virus results in packaging of the rAAV genomes as infectious rAAV particles. A presently preferred stable cell line is the A64 HeLa cell line which was deposited with the ATCC on Jun. 1, 1994 and was assigned ATCC Accession No. CRL 11639. The present invention also provides stable cell lines containing AAV rep and cap sequences but no rAAV genome.

Recombinant AAV generated by the foregoing packaging process are useful for delivering the DNA of interest to cells. In vivo, rAAV may be used as antisense delivery vectors, gene therapy vectors or vaccine (i.e., genetic immunization) vectors. Treatment of disease conditions including, for example, AIDS; neurological disorders including cancer, Alzheimer's disease, Parkinson's disease, Huntington's disease, and autoimmune diseases such as multiple sclerosis, trauma, depresssion, migraine, pain or seizure disorders; adult T-cell leukemia; tropical spastic paraparesis; upper and lower respiratory tract infections; upper and lower respiratory tract infections; measles; mumps; rubella; polio; influenza; influenza; hepatitis; hepatitis; hepatitis; hepatitis; hepatitis; diarrhea; diarrhea; systemic cytomegalovirus infections; mononucleosis-likeillness; systemic Epstein-Barr virus infections; classic infectious mononucleosis; systemic herpes simplex types 1 and 2 infections; genital herpes simplex infections; chickenpox; roseola; febrile illness due to human herpes virus type 6; pneumonia and adult respiratory distress syndrome; upper and lower respiratory tract infections; conjunctivitis; upper and lower respiratory tract infections; upper and lower respiratory tract infections; genital tract infections; upper and lower respiratory tract infections; pulmonary and extrapulmonary tuberculosis; systemic infections due to atypical mycobacteria; feline leukemia; feline AIDS; bovine AIDS; equine infectious anemia; arthritis and encephalitis in goats; and pneumonia and encephalitis in sheep are contemplated by the invention. As a vaccine vector, rAAV delivers a gene of interest to a cell and the gene is expressed in the cell. The vaccine vectors may be used to generate intracellular immunity if the gene product is cytoplasmic (e.g., if the gene product prevents integration or replication of a virus). Alternatively, extracellular/systemic immunity may be generated if the gene product is expressed on the surface of the cell or is secreted.

A host (especially a human host) may be immunized against a polypeptide of a disease-causing organism by administering to the host an immunity-inducing amount of a rAAV of the invention which encodes the polypeptide. Immunization of a human host with a rAAV of the invention involves administration by inoculation of an immunity-inducing dose of the virus by the parenteral route (e.g., by intravenous, intramuscular or subcutaneous injection), by surface scarification or by inoculation into a body cavity. Typically, one or several inoculations of between about 1000 and about 10,000,000 infectious units each, as measured in susceptible human or nonhuman primate cell lines, are sufficient to effect immunization of a human host. Virus to be used as a vaccine may be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of a rAAV of the invention which encodes the polypeptide is administered to a host in need of such treatment. The use of rAAV of the invention in the manufacture of a medicament for inducing immunity in, or providing gene therapy to, a host is contemplated.

BRIEF DESCRIPTION OF THE DRAWING

Numerous other aspects and advantages of the present invention will be apparent upon consideration of the following detailed description thereof, reference being made to the drawing wherein.

DETAILED DESCRIPTION

The present invention is illustrated by the following examples relating to the production and use of rAAV of the invention. Example 1 describes the construction of a vector including a rAAV genome containing the SIV rev and envelope (gp160) genes, while Example 2 describes the construction of a vector including the AAV rep-cap genes and a neomycin resistance gene. Example 3 sets out the construction of a vector to be used to generate stable cell lines producing rAAV from the vectors described in Examples 1 and 2. The generation of stable cell lines producing rAAV encoding the SIV rev and gp160 proteins is detailed in Example 4. Example 5 describes the generation of stable cell lines expressing the AAV rep-cap genes. Example 6 presents results of infection of various mammalian cells and cell lines with the rAAV described in Example 4 which show that gp160 protein is expressed in the infected cells.

EXAMPLE 1

Figure 1:
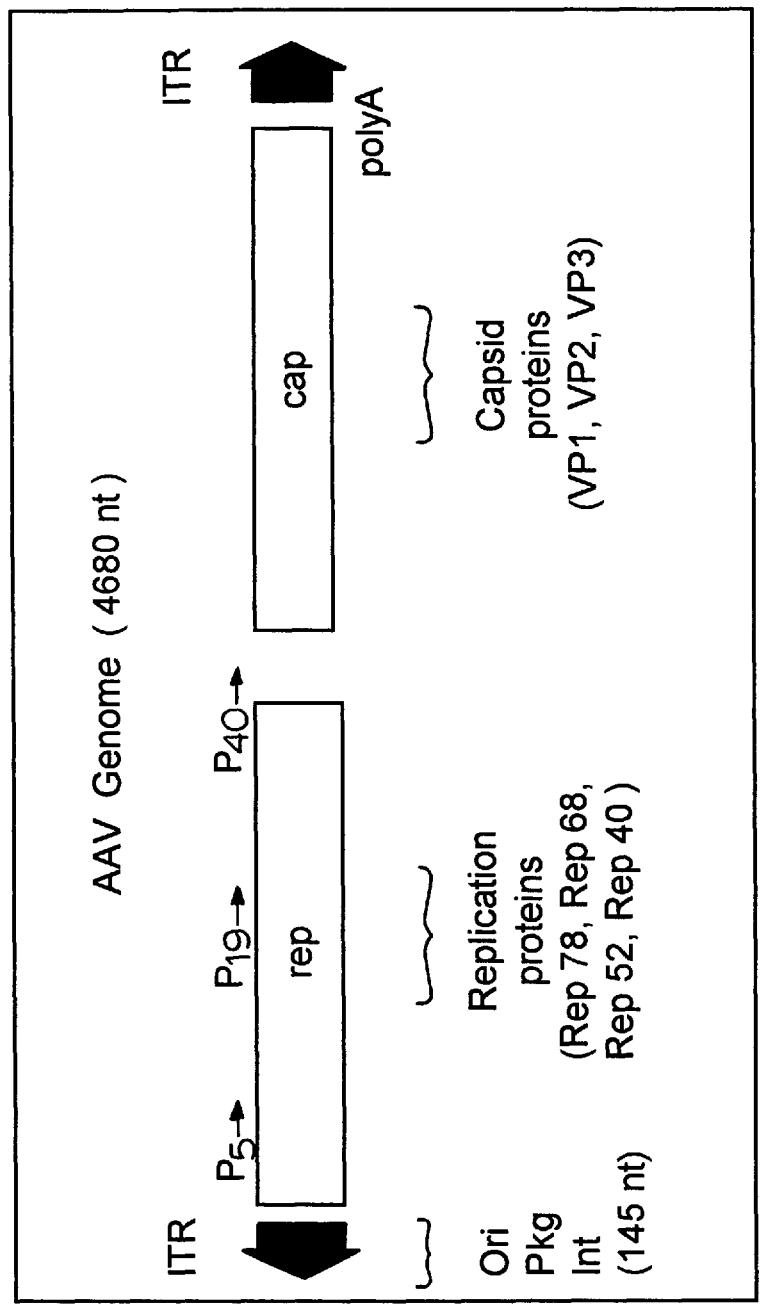
FIG. 1 is a schematic representation of the AAV genome.
Figure 2:
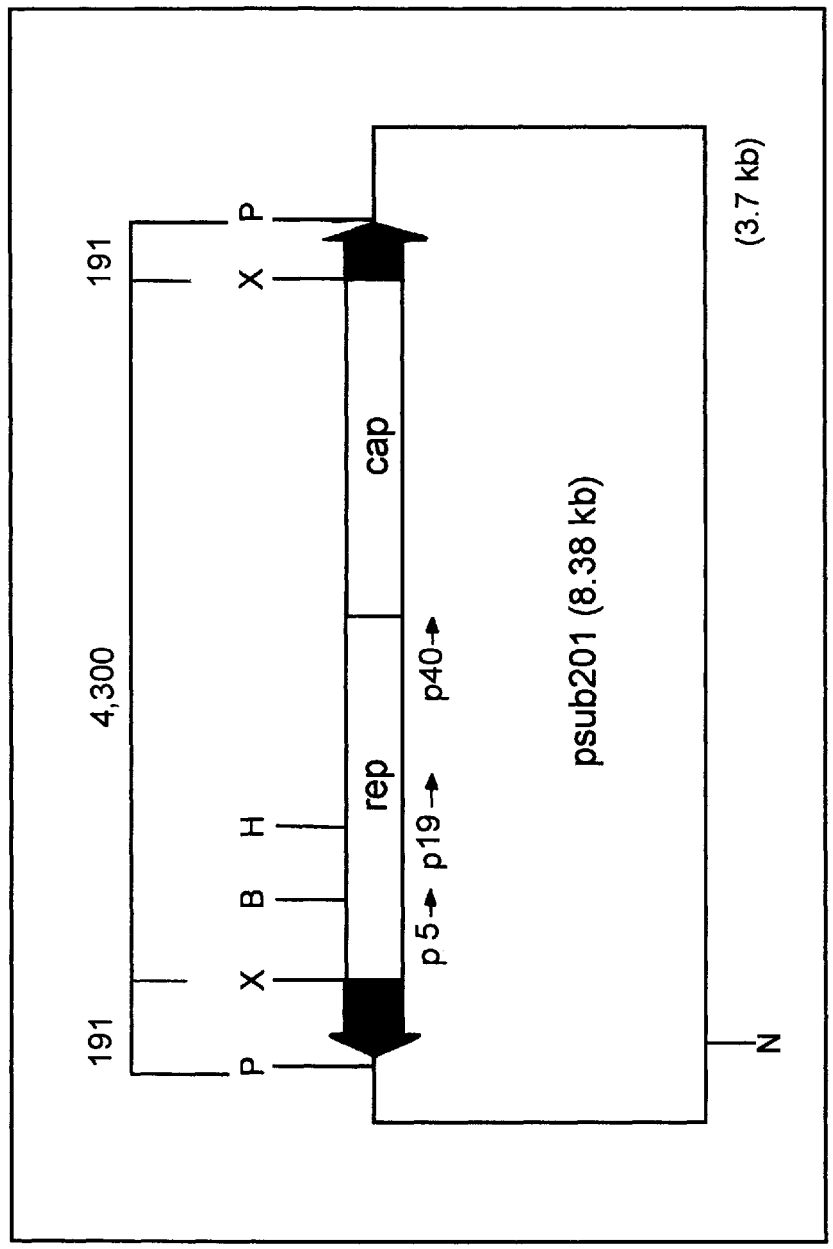
FIG. 2 is a schematic representation of plasmid psub201 which was the source of AAV2 sequences utilized in the examples.

A vector including a rAAV genome containing a SIV rev and envelope (gp160) gene cassette was constructed from an existing plasmid designated psub201 [Samulski et al., supra]. FIG. 2 is a diagram of plasmid psub201 wherein restriction endonuclease sites are shown and abbreviated as follows: P, PvuII; X, XbaI; B, BamHI; H, HindIII; and N, NaeI. The plasmid contains a modified wild-type AAV2 genome cloned between the PvuII restriction sites. The DNA sequence of the wild-type AAV2 genome is set out in SEQ ID NO: 1. The AAV2 sequence was modified to include convenient restriction sites. Specifically, two XbaI restriction sites were added via linker addition at sequence positions 190 and 4484. These sites are internal to 191 bp inverted terminal repeats (ITRs) which included the 145 bp ITRs of the AAV genome. The insertion of these sites allows the complete removal of the internal 4.3 kb fragment containing the AAV rep-cap genes upon XbaI digestion of the plasmid. In FIG. 2, the 191 bp ITRs are designated by inverted arrows.

The rAAV genome vector of the invention (pAAV/CMV/SIVrev-gp160) was generated in several steps.

First, plasmid psub201 was digested with XbaI and the approximately 4 kb vector fragment including the AAV ITRs was isolated. A CMV gene expression cassette was then inserted between the AAV ITRs by blunt end ligation. The CMV expression cassette was derived as a 1.8 kb XbaI - AflIII DNA fragment from the vector pCMV-NEO-BAM described in Karasuyama et al., *J. Exp. Med.*, 169: 13–25 (1989). Prior to ligation, the molecular ends were filled in using the Klenow fragment of DNA polymerase I. The CMV expression cassette contained a 750 bp portion of the CMV immediate early promoter, followed by a 640 bp intron and a 360 bp polyadenylation signal sequence which were derived from the rabbit β-globin gene. Between the intron and poly A sequences were two cloning sites: a unique BamHI site and two flanking EcoRI restriction sites. The resulting vector was named pAAV/CMV. See FIG. 3A wherein restriction endonuclease cleavage sites are shown and abbreviated as follows: B, BamHI; E, EcoRI ; N, NaeI; and P, PvuII.

Second, the pAAV/CMV expression vector was linerized at the BamHI site and sticky ends were blunted with Klenow. A PCR-generated, 2.7 kb SIV subgenomic fragment containing the rev and envelope (gp160) sequences [SEQ ID NO: 2, Hirsch et al., *Nature*, 339: 389–392 (1989)] was cloned into the blunt-ended BamHI site. The resulting recombinant AAV genome vector, pAAV/CMV/SIVrev-gp 160, is 8.53 kb in length. See FIG. 3B wherein restriction endonuclease cleavage sites are shown and abbreviated as follows: N, NaeI and P, PvuII. The vector contains the following DNA segments in sequence: (1) an AAV ITR, (2) the CMV promoter, (3) the rabbit β-globin intron, (4) the SIV rev and envelope sequences, (5) the rabbit β-globin polyadenylation signal, and (6) an AAV ITR. In transient transfection assays of human 293 cells, this vector resulted in high levels of expression of the SIV gp160 protein as determined by radioimmunoprecipitation assays using polyclonal sera from monkeys infected with SIV.

The invention specifically contemplates substitution by standard recombinant DNA techniques of the following sequences for the SIV rev/envelope sequences in the foregoing vector: HIV-1 rev/envelope sequences (the HIV-1$_{MN}$ rev/envelope sequence is set out in SEQ ID NO: 3); nerve growth factor [Levi-Montalcini, *Science,* 237: 1154–1162 (et al.,)]; ciliary neurotrophic factor [Manthorpe et al., beginning at p. 135 in *Nerve Growth Factors*, Wiley and Sons (1989)]; glial cell derived neurotrophic factor [Lin et al., *Science,* 260: 1130–1132 (1993)]; transforming growth factors [Puolakkainen et al., beginning at p. 359 in *Neurotrophic Factors*, Academic Press (1993)]; acidic and basic fibroblast growth factors [Unsicker et al., beginning at p. 313 in *Neurotrophic Factors*, Academic Press (1993)]; neurotrophin 3 [Maisonpierre et al., *Genomics,* 10: 558–568 (1991)]; brain-derived neurotrophic factor [Maisonpierre, supra]; neurotrophin 4/5 [Berkemeier et al., *Neuron,* 7: 857–866 (1991)]; tyrosine hydroxylase [Grima et al., *Nature,* 326: 707–711 (1987)]; and aromatic amino acid decarboxylase [Sumi et al., *J. Neurochemistry,* 55: 1075–1078 (1990)].

EXAMPLE 2

A plasmid designated pSV40/neo/rep-cap which contains the AAV rep-cap genes and a neomycin resistance gene was constructed to be used in conjunction with the rAAV genome vector described in Example 1 to generate a stable cell line producing rAAV.

Figure 4:
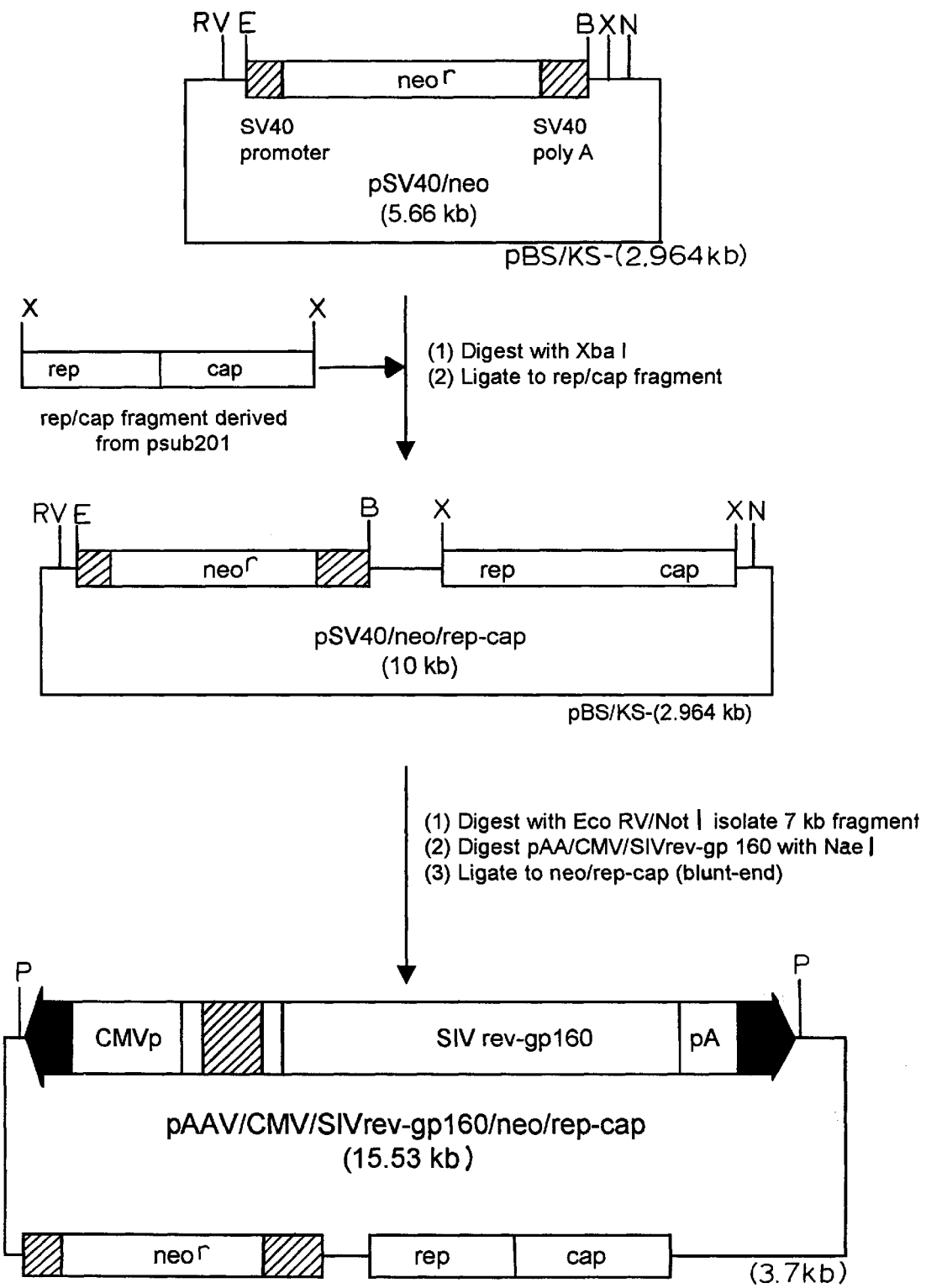
FIG. 4 is a flow diagram of the construction of the vector pAAV/CMV/SIVrev-gp160/neo/rep-cap useful to generate a stable cell line producing rAAV of the invention.

A plasmid designated pAAV/SVneo (Samulski et al., supra) was digested with EcoRI and BamHI to release a 2.7 kb insert including a 421 bp portion of the SV40 early promoter, a 1.4 kb neomycin resistance gene, and a 852 bp DNA fragment containing the SV40 small t splice site and SV40 polyadenylation signal. This released insert was cloned into the EcoRI and BamHI sites of pBLUESCRIPT KS+ (Stratagene, La Jolla, Calif.) to generate the 5.66 kb plasmid pSV40/neo. Next, the approximately 4.3 kb DNA fragment containing the AAV rep-cap genes, derived from the digestion of psub201 with XbaI as described in Example 1, was ligated into the XbaI restriction site of pSV40/neo to create the plasmid pSV40/neo/rep-cap (about 10 kb). The construction of this plasmid is detailed in first half of FIG. 4 wherein restriction endonuclease sites are shown and abbreviated as follows: B, BamHI; E, EcoRI; HindIII; P, PvuII; N, NotI; RV, EcoRV; and X, XbaI. This plasmid was functional in transient assays for rep and cap activity and was itself ultimately used to derive stable cell lines (see Example 5 below).

EXAMPLE 3

A final vector to be used to generate stable cell lines producing rAAV was generated from vector pAAV/CMV/SIVrev-gp160 (Example 1) and plasmid pSV40/neo/rep-cap (Example 2).

Figure 3:
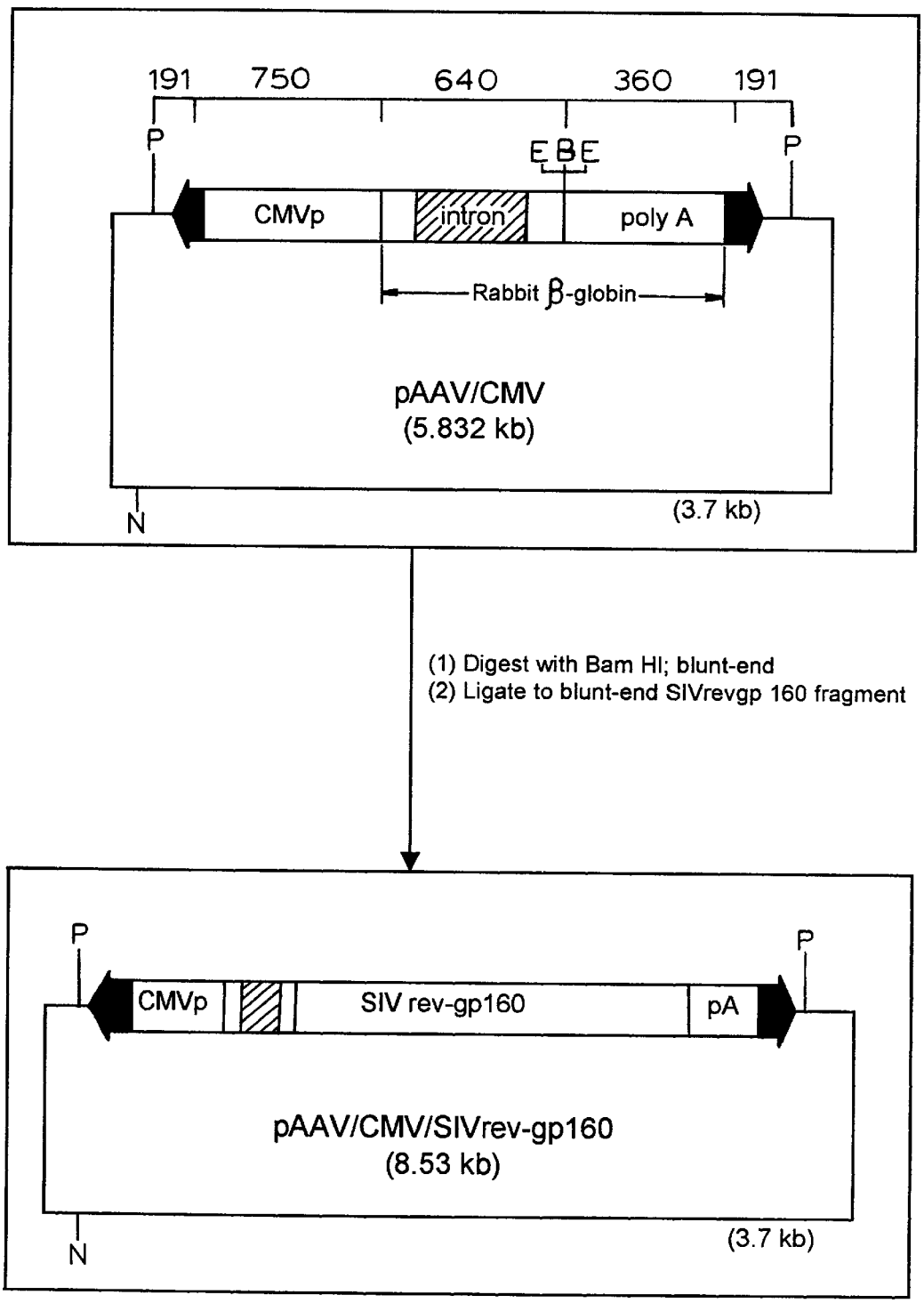
FIG. 3 is a flow diagram of the construction of a rAAV genome of the invention in vector pAAV/DMV/SIVrev-gp160.

The construction entailed removing the neo-rep-cap gene cassette from pSV40/neo/rep-cap and inserting it into a unique NaeI site in pAAV/CMV/SIVrev-gp160 (see FIG. 3B). Specifically, vector pAAV/CMV/SIVrev-gp160/neo/rep-cap was made by agarose gel band isolating a 7.0 kb EcoRV-NotI DNA fragment containing the SV/neo and rep-cap expression domains from pSV40/neo/rep-cap. The sticky ends of the fragment were blunted with Klenow and the fragment was ligated into the blunt-ended NaeI site of pAAV/CMV/SIVrev-gp160. See FIG. 4. Vector pAAV/CMV/SIVrev-gp160/neo/rep-cap (ATCC 6963contains the following elements: (1) the rAAV genome; (2) AAV rep-cap genes; and (3) the neomycin resistance gene.

EXAMPLE 4

The vector pAAV/CMV/SIVrev-gp160/neo/rep-cap was used to generate stable cells lines containing both the rAAV genome of the invention and AAV rep-cap genes.

HeLa cells at 70% confluency were transfected with 10 μg of pAAV/CMV/SIVrev-gp160/neo/rep-cap plasmid DNA in 100 mm dishes. Cells were transfected for 6 hours after formation of DOTAP/DNA complexes in serum minus media as prescribed by the manufacturer's protocol (Boehringer-Mannheim, Indianapolis, Ind.). Following the removal of the transfection medium, DMEM media containing 10% fetal bovine serum was added to the cells. Three days later, media supplemented with 700 μg/ml Geneticin (Gibco-BRL, Gaithersburg, Md.) was used to select for cells that stably expressed the neomycin resistance gene. Fresh Geneticin containing DMEM media was added every four days. Geneticin resistant clones were selected 10–14 days after selective media was added. A total of fifty-five colonies were selected and transferred to 24-well plates and expanded for further analysis.

Figure 5:
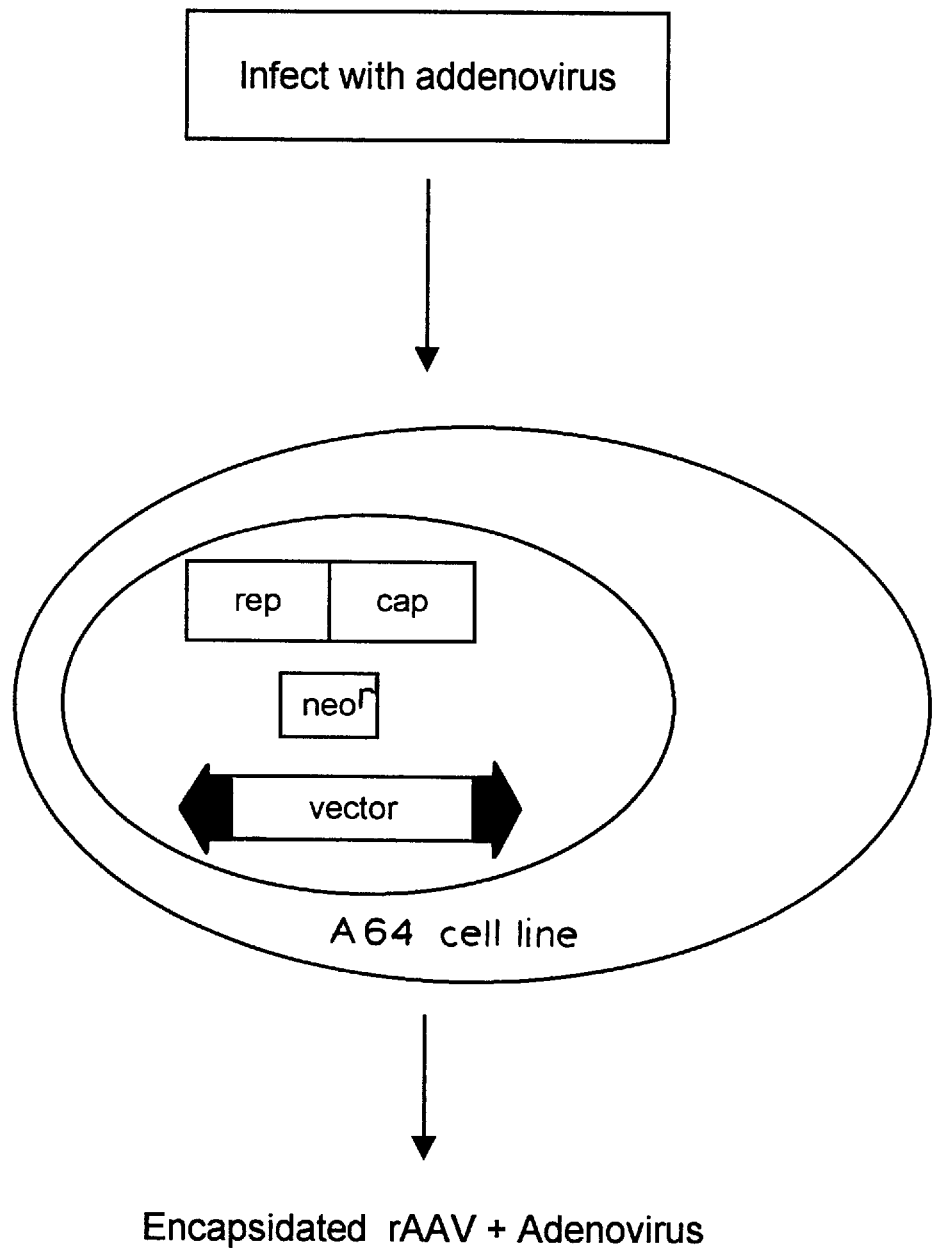
FIG. 5 is a schematic representation of a method for packaging rAAV utilizing stable host cell lines of the invention.

The fifty-five neomycin resistant HeLa cell lines were initially screened for functional rep gene activity; twenty-one scored positive. Rep gene activity was assayed by infecting the cell lines with adenovirus type 5 (Ad5). Infection by adenovirus transactivates the rep and cap genes. This results in the replication of the rAAV genome and subsequent encapsidation of these sequences into infectious rAAV particels. A schematic representation of rAAV production is shown in FIG. 5. Following maximum Ad5-induced cytopathic effect (CPE; rounding of cells and 90% detachment from the culture flask), cell lysates were prepared and Hirt DNA (low molecular weight DNA) was isolated [Hirt, *J. Mol. Biol.,* 26: 365–369 (1967)]. Southern blot analysis was used to visualize the synthesis of recombinant AAV (rAAV) replicative forms (single strand, monomeric, and dimeric forms). Control wells not receiving Ad5 were always negative. Cell lines with high relative levels of rep gene activity were selected for further study.

To assay for cap gene functionality, cell lines were infected with Ad5 and clarified lysates prepared after the development of maximum CPE. The cell lysates, Ad5, and wild-type AAV were used to infect HeLa cells. Following the development of Ad5 induced CPE (72 hr), Hirt DNA was isolated and Southern blot analysis performed. Cell line lysates that gave rise to gp160 hybridizable rAAV (SIV gp160) replicative sequences were scored positive for capsid production.

An infectious unit/ml (IU/ml) titer of rAAV produced by each cell line was derived by co-infecting C12 cells (exhibiting stable rep and cap gene expression) with Ad5 and a serial ten-fold dilution of the clarified cell line lysate to be tested. After maximum Ad5-induced CPE, Hirt DNA was isolated and Southern blot analysis performed to detect the presence of rAAV replicative forms. The end-point dilution that produced visible monomeric and dimeric replication intermediates was taken as the titer. Titer estimation was based on two to four replicate experiments.

Results of characterization of eight of the fifty-five cell lines are shown in Table 1 below wherein "ND" indicates a value was not determined.

TABLE 1

| Cell Line | Rep Function | Cap Function | Titer (IU/ml) |
| --- | --- | --- | --- |
| A5  | ++    | + | $10^4$ |
| A11 | ++++  | + | $10^5$ |
| A15 | ++++  | + | $10^5$ |
| A37 | ++++  | + | ND |
| A60 | +++++ | − | $<10^1$ |
| A64 | +++++ | + | $10^6$ |
| A69 | ++    | − | ND |
| A80 | ++++  | + | $10^5$ |

Cell line A64 (ATCC CRL 11639) produced a high titer of rAAV ($10^6$ iu/ml) in clarified lysates. This titer is approximately 1000-fold higher than the titer of rAAV reported by Vincent et al., supra.

The rAAV produced by the various cell lines was also tested for its ability to express SIV gp160 in HeLa cells infected with the recombinant virus. Concentrated stocks of rAAV produced by the eight stable cell lines listed in Table 1 were generated. Cell lysates containing rAAV particles were subjected to step density gradient (CsCl) purification. After desalting dialysis and heat-inactivation of Ad5, the rAAV particles were used to infect (transduce) HeLa cells in culture. Two lines of investigation were pursued. First, the transduced cells were tested for the presence of SIV gp160-specific mRNA by performing RT-PCR on total RNA collected 72 hours after transduction. Primers specific for SIV gp160 amplified a predicted 300 bp fragment only in the presence of reverse transcriptase and Taq polymerase; samples run without reverse transcriptase were uniformly negative. Second, HeLa cells were transduced with various dilutions of the same rAAV/SIV stock as described above and, at 72 hours post transduction, indirect immunofluorescence was performed on the infected cells. At all dilutions tested (out to 1:200), cells positive for the SIV gp160 protein were detected; lower dilutions clearly had more positive cells.

The A64 cell line was tested for wild-type AAV production by a standard method. The cell line was infected with adenovirus to produce rAAV as a lysate. The lysate was then used to infect normal HeLa cells either: (i) alone; (ii) with adenovirus; or (iii) with adenovirus and wild-type AAV. As a control, HeLa cells were infected with adenovirus and wild-type AAV without rAAV. Hirt DNA was prepared and analyzed by Southern blotting (two different blots) for replicating forms of either rAAV or wild-type AAV. No wild-type AAV was detected in A64 cells not exposed to wild-type AAV.

Because the present invention involves the establishment of stable cell lines containing not only copies of the AAV rep and cap genes, but also of the rAAV genome (with ITRs flanking DNA of interest), rAAV is produced by merely infecting the cell line with adenovirus. Transfection of exogenous DNA is not required, thereby increasing the efficiency of rAAV production compared to previously described methods. Other significant features of the invention are that no wild-type AAV is produced and that scale-up for production of rAAV is easy and is limited only by normal constraints of cell growth in culture.

EXAMPLE 5

Concurrent with the generation of the stable cells described in Example 4, stable HeLa cell lines were established by similar methods which contained rep-cap genes but no rAAV genome using plasmid pSV40/neo/rep-cap (Example 2). A total of fifty-two neomycin resistant HeLa cell lines were isolated and characterized.

To test for rep gene function, each cell line was infected with Ad5 and subsequently transfected with pAAV/CMV/SIVrev-gp160. Following Ad5-induced CPE (72 hr), Hirt DNA was isolated and Southern blot analysis performed. Rep gene function was scored positive for cell lines that produced monomeric and dimeric rAAV gp160 sequences. The intensity of autoradiographic signal was used as a relative measure of rep gene expression (1–5+). Ad5 minus control samples never produced rAAV replicative forms. Cap gene proficiency was assayed in a similar manner (Ad5 infection and pAAV/CMV/SIVrev-gp160 transfection), except that a clarified cell lysate was prepared after the development of maximum CPE. HeLa cells were then co-infected with a portion of the clarified cell lysate, Ad5, and wild-type AAV. Hirt DNA was isolated 72 hours later, and hybridization analysis was used to visualize the existence of rAAV/gp160 replicative forms (monomeric and dimeric). In the assay described, the C12 cell line yielded the highest relative proportion of rAAV/gp160/120 sequences.

Results of the characterization assays are presented for eight cell lines are presented in Table 2 wherein the abbreviation "ND" indicates that a value was not determined.

TABLE 2

| Cell Line | Rep Function | Cap Function |
| --- | --- | --- |
| C2  | +++++ | + |
| C12 | ++++  | +++ |
| C16 | −     | ND |
| C18 | +++   | ND |
| C23 | +++   | ND |
| C25 | +++   | − |
| C27 | ++    | ND |
| C44 | ++++  | + |

There are two principal uses for the stable cell lines expressing rep-cap sequences: (1) generating rAAV particles if the cell lines are transfected with a rAAV genome and infected with helper virus; and (2) determining rAAV infectious titers. To estimate rAAV infectious titers, these cell lines are co-infected with adenovirus and serial dilutions of the rAAV stock. After maximum CPE, Hirt DNA is isolated and replicative rAAV forms are visualized by Southern blot analysis. End point titration (last rAAV stock dilution to give positive hybridization signal) is then used to determine the infectious titer.

EXAMPLE 6

The ability of the rAAV produced by HeLa cell line A64 to infect (transduce) and produce SIV gp160 protein in various mammalian cell types in addition to HeLa cells (see Example 4) was assayed. The rAAV (at a multiplicity of infection of approximately 1) was used to infect cells either in a monolayer or in suspension, depending on the cell type. Three days after rAAV infection, the cells were fixed in acetone/methanol and evaluated for the production of gp160 by indirect immunofluorescence using polyclonal antisera from an SIV-infected monkey. The following cells or cell lines were infected and shown to produce gp160; fetal rat brain cells (neurons and glial cells), mouse 3T3 fibroblasts, mouse vagina, human vagina, human colon, human and monkey lymphocytes and 293 cells. No non-permissive cell type was identified. These results demonstrate that the rAAV produced by the A64 cell line infects a wide range of mammalian cell types and leads to cell surface expression of the SIV envelop gene product, gp160, in the transduced cells.

While the present invention has been described in terms of preferred embodiments, it understood that variations and improvements will occur to those skilled in the art. Therefore, only such limitations as appear in the claims should be placed on the invention.

What is claimed is:

1. A DNA vector comprising a recombinant adeno-associated virus genome and DNA sequences encoding adeno-associated rep/cap proteins, wherein said recombinant adeno-associated virus genome comprises adeno-associated virus inverted terminal repeats flanking non-adeno-associated virus DNA sequences operably linked to promoter and polyadenylation sequences and wherein said DNA sequences encoding rep/cap proteins are located outside said genome.

2. The DNA vector of claim 1 wherein said non-adeno-associated virus DNA sequences are DNA sequences encoding an immunodeficiency virus protein.

3. The DNA vector of claim 1 wherein said non-adeno-associated virus DNA sequences are DNA sequences encoding a polypeptide selected from the group consisting of tyrosine hydroxylase, aromatic amino acid decarboxylase, nerve growth factor, brain derived neurotrophic factor, NT-3,NT-4/5, glial derived growth factor and fibroblast growth factor.

4. The DNA vector of claim 2 which is vector pAAV/CMV/SIVrev-gp 160/neo/rep-cap (ATCC 69637).

* * * * *

UNITED STATES PATENT AND TRADEMARK OFFICE
CERTIFICATE OF CORRECTION

PATENT NO.    : 5,858,775
DATED         : January 12, 1999
INVENTOR(S)   : Philip R. Johnson It is certified that error appears in the above-identified patent and that said Letters Patent is hereby corrected as shown below:

Column 2,
Line 16, replace "virus-i" with -- virus-1 --.
Line 38, replace "reletively" with -- relatively --.

Column 3,
Line 15, replace "requires" with -- require --.

Column 4,
Line 6, replace "enoding" with -- encoding --.
Line 18, replace "supressor" with -- suppressor --.
Lines 62-63, after "infection;" and before "measles" delete "upper and lower respiratory tract infections;".
Line 64, after "influenza;" and before "hepatitis" delete "influenza".
Lines 64-65, after "hepatitis;" and before "diarrhea" delete "hepatitis; hepatitis; hepatitis; hepatitis;".

Column 5,
Lines 4-5, after "syndrome;" and before "conjunctivitis" delete "upper and lower respiratory tract infections;".
Lines 5-6, after "conjunctivitis;" and before "genital" delete "upper and lower respiratory tract infections; upper and lower respiratory tract infections;".
Lines 7-8, after "infections;" and before "pulmonary" delete "upper and lower respiratory tract infections;".

Column 7,
Lines 15-16, after "1154-1162" and before "]" delete "(et al.,)".
Lines 15-16, replace "(et al.,)" with -- (1987) --.

Column 8,
Line 11, replace "6963contains" with -- 69637) contains --.
Line 46, replace "particels" with -- particles --.

UNITED STATES PATENT AND TRADEMARK OFFICE
CERTIFICATE OF CORRECTION

PATENT NO.    : 5,858,775
DATED         : January 12, 1999
INVENTOR(S)   : Philip R. Johnson It is certified that error appears in the above-identified patent and that said Letters Patent is hereby corrected as shown below:

Column 12,
Line 8, replace "envelop" with -- envelope --.
Line 11, after "it" and before "understood" insert -- is --.

Signed and Sealed this

Twenty-ninth Day of July, 2003

JAMES E. ROGAN
*Director of the United States Patent and Trademark Office*